United States Patent [19]

Foley et al.

[11] 4,308,349

[45] Dec. 29, 1981

[54] ISOMERIZATION OF GLUCOSE TO FRUCTOSE USING GLUCOSE ISOMERASE FROM AMPULLARIELLA

[75] Inventors: Sharonkay E. Foley, Lafayette, Colo.; Patrick J. Oriel; Carol C. Epstein, both of Midland, Mich.

[73] Assignee: The Dow Chemical Company, Midland, Mich.

[21] Appl. No.: 884,925

[22] Filed: Mar. 9, 1978

[51] Int. Cl.$^3$ .................. C12P 19/24; C12N 9/92; C12N 1/20; C12R 1/01
[52] U.S. Cl. .................................. 435/94; 435/234; 435/253; 435/822
[58] Field of Search ............... 435/94, 234, 253, 172, 435/822

[56] References Cited

U.S. PATENT DOCUMENTS

| | | | |
|---|---|---|---|
| 3,625,828 | 12/1971 | Brownewell | 435/234 |
| 3,708,397 | 1/1973 | Sipos | 435/94 |
| 3,826,714 | 7/1974 | Suekane et al. | 435/94 |
| 3,829,362 | 8/1974 | Horwath et al. | 435/94 |
| 3,834,988 | 9/1974 | Shiek | 435/94 |
| 3,956,066 | 5/1976 | Coker et al. | 435/94 |
| 3,957,587 | 5/1976 | Armbruster et al. | 435/94 |
| 4,009,074 | 2/1977 | Walon | 435/94 |

OTHER PUBLICATIONS

Buchanan et al., *Bergey's Manual of Determinative Bacteriology*, 8th ed., The Williams & Wilkins Co., Baltimore (1974), pp. 716–718.

Hamilton, et al, "Glucose Isomerase a Cast Study of Enzyme-Catalzed Process Technology", *Immobilized Enzymes in Food and Microbial Processes*, Olson et al., etc., Plenum Press, New York, (1974), pp. 94–106, 112, 115–137.

Chem, etal., "Glucose Isomerase (a Review)", *Process Biochem., (1980), pp. 30–35.*

Chem, et al., "Glucose Isomerase (a Review),"*Process Biochem, (1980), pp. 36–41.*

Couch, "Some New Genera and Species of the Actinoplanaceae", *J. of the Mitchell Soc.*, (May 1963), pp. 53–70.

Nordahl et al., "Fructose Manufacture from Glucose by Immobilized Glucose Isomerase", *Chem. Abstracts*, vol. 82, (1975), Abs. No. 110316h.

Takasaki, "Fructose Production by Glucose Isomerase", *Chem. Abstracts*, vol. 81, (1974), Abs. No. 76474a.

*Primary Examiner*—Thomas G. Wiseman

[57] ABSTRACT

The production of a heat stable glucose isomerase from a microorganism belonging to the genus Ampullariella and a method for using the isomerase to convert glucose to fructose.

27 Claims, No Drawings

ISOMERIZATION OF GLUCOSE TO FRUCTOSE USING GLUCOSE ISOMERASE FROM AMPULLARIELLA

BACKGROUND OF THE INVENTION

Glucose and fructose are the monosaccharides which are liberated upon the hydrolysis of sucrose. Glucose, also known as dextrose, is an aldohexose which is produced commercially from starch, especially corn starch, by the food processing industry. Fructose, also called levulose, is a ketohexose which is not present in significant concentrations in starch-derived syrups and sugars. However, because fructose is sweeter than glucose, it is desirable to convert at least part of the glucose in the starch-derived syrup or sugar to fructose to give the product the taste characteristics of cane or beet sugar. The isomerization of glucose to fructose may be accomplished by the use of various alkaline catalysts or by means of an enzymatic conversion. Alkaline catalysis, although widely used in the past, gives rather low yields and also produces undesirable by-products which effect the quality of the syrup. As a result of these drawbacks, enzymatic conversions using a glucose isomerase have become increasingly popular.

A number of glucose isomerases have been isolated from different species of microorganisms. Glucose isomerase has been produced by microorganisms from the generae Streptomyces, Actinoplanes, Bacillus, Flavobacterium, Brevibacterium, Arthrobacter, Nocardia, Micromonospora, Microbispora, and Microellobospora. Disadvantages of using an enzyme conversion of glucose to fructose reside in the cost of producing the enzyme and the sensitivity of the enzyme to environmental parameters. Isomerase preparations are usually inactivated by higher temperatures, so relatively low temperatures must be used to carry out the isomerization. Thus, longer overall reaction times are necessary than would be required if the isomerization could be carried out at a higher temperature. In addition, immobilization techniques necessary to recover the isomerase during processing are limited to those employing only mild temperature conditions. Therefore, a glucose isomerase having good heat stability is especially preferred.

SUMMARY OF THE INVENTION

The present invention is directed to a method of producing glucose isomerase from a microorganism belonging to the genus Ampullariella which comprises growing the Ampullariella in a culture medium and recovering the glucose isomerase therefrom. The glucose isomerase produced using this method has demonstrated superior thermal stability. Samples of the isomerase derived from some strains have been shown to retain essentially all of their original activity after heating at 75° C. for a period of 24 hours.

The present invention is also directed to a process for converting D-glucose to D-fructose which includes the step of treating an aqueous solution containing glucose with an isomerase produced by a microorganism belonging to the genus Ampullariella thereby converting a portion of the glucose to fructose.

Due to the difficulty of isolating members of the genus only four species of Ampullariella had been previously described in the literature. See *Jour. of the Mitchell Soc.*, May 1963, page 53. Known species include *Ampullariella lobata*, *Ampullariella digitata*, *Ampullariella campanulata*, and *Ampullariella regularis*. All the known species have been found to produce glucose isomerase. In addition, new organisms belonging to the genus have been isolated and found to produce glucose isomerase. These isolates although belonging to the genus Ampullariella cannot be placed into any of the known species within the genus, and therefore represent previously unknown species of Ampullariella. These novel isolates are referred to herein as Ampullariella species 3876 (ATCC 31351), Ampullariella species 3877 (ATCC 31352), Ampullariella species 3965 (ATCC 31353), and Ampullariella species 3966 (ATCC 31354). Especially preferred for the production of glucose isomerase is the novel species Ampullariella species 3876, the enzyme of which has demonstrated superior heat stability. Mutant microorganisms derived from the species disclosed herein and capable of producing glucose isomerase are considered as being within the scope of the invention. Subcultures of the previously unknown isolates have been made part of the permanent collection of the American Type Culture Collection, 12301 Parklawn Dr., Rockville, Md.

DETAILED DESCRIPTION OF THE INVENTION

The genus Ampullariella is characterized as having rod-shaped zoospores, 0.3–0.7 by 0.8 to 1.5 μm, with a single polar flagellum or from one to two lateral flagella. The agar colonies are generally yellow-brown, yellow-grey, yellow or bright lemon yellow. The most distinctive feature of the genus are the predominantly cylindrical sporangia and the zoospores which are generally arranged end to end in longitudinal rows within the sporangia. Normally, the organisms grow saprophytically on a variety of plant and animal material, especially on hair and other keratinous matter. They are found in soils.

Ampullariella are aerobic and grow well on various nutrient medium which contain an assimilable source of nitrogen, an assimilable source of carbon, and essential minerals. Although for the production of glucose isomerase it is preferred that the culture medium contain xylose, the isomerase will be produced in lesser amounts in the absence of xylose. The amount of xylose required in the medium to give satisfactory enzyme production for commercially recoverable quantities are generally between about 0.1 percent and 10 percent by weight. Members of the genus generally grow best at temperatures between about 15° C. and 45° C. The glucose isomerase is produced intracellularly and is generally not excreted into the surrounding culture medium. To isolate the isomerase it is, therefore, necessary to disrupt the cell walls to release the enzyme. Disruption of the cell walls may be accomplished by techniques well known in the art, such as, for example, by ultrasonic rupture.

As recognized by one skilled in the art, the conversion of D-glucose to D-fructose using the glucose isomerase produced above is generally carried out in an aqueous medium. Aqueous solution useful in the isomerization of glucose, as for example corn syrup, may contain from about 5 percent to 80 percent glucose by weight, with about 30 percent to 60 percent being preferred. The final fructose concentration of the isomerized solution will depend on a number of factors well understood in the art, such as for example the amount of glucose isomerase used, the period of treatment, the temperature employed, pH of the solution, etc. In addition, as the equilibrium between the aldo and keto hexoses is approached the rate of isomerization will decrease; therefore, the process is generally terminated when the percent weight of fructose is between about 40 to 50 percent of the total combined dry weight of glucose and fructose.

Pursuant to the present invention, the syrup may be treated with glucose isomerase using either a batch or continuous process. In either case, it is generally preferred that the enzyme be immobilized by a water-insoluble support, usually a polymer, either by physical absorption covalent bonding, or by entrapment. In the first two methods of immobilization, a glucose isomerase/water-insoluble polymer conjugate is formed which makes retention and recycling of the enzyme possible. Conjugates formed by the covalent bonding of the isomerase to the water-insoluble polymer include conjugates resulting from the reaction between the isomerase and a water-insoluble, functionalized polymer; the incorporation of the isomerase into a growing polymer chain; or the intermolecular crosslinking of the enzyme with a multifunctional, low molecular weight reagent. Synthetic supports which have been used for covalently bonding to enzymes and which would be suitable for use with the present invention include polymers based upon acrylamide, maleic anhydride, methacrylic acid, and styrene. Well known natural supports include agarose, cellulose, dextran and starch. Commonly used adsorbents which have been used to immobilize enzymes include alumina, ion-exchange resins, calcium carbonate, carbon, cellulose, clays, collagen, collodion, conditioned metal or glass surfaces, diatomaceous earth, hydroxylapatite and the like. Various methods of forming such glucose isomerase/water-insoluble polymer conjugates are discussed in texts such as *Immobilized Enzymes,* by O. Zaborky (CRC Press, Ohio) 1973. See also U.S. Pat. Nos. 3,519,538; 3,788,945; 3,933,587; and 3,933,589.

Another suitable method for the immobilization of the glucose isomerase is by use of a hollow fiber reactor. This type of system may be preferable to immobilization on an active support where the possibility of active chemical residues should be avoided, as for example in the production of foodstuffs. See *Jour. of Food Science* 42, 258 (1977).

It is understood that the amount of glucose isomerase employed in the isomerization of the syrup can vary considerably. Although greater or lesser amounts of glucose isomerase may be used in carrying out the method of this invention, in practice productivity ranges of between about 50 pounds and 5000 pounds of fructose/glucose mixture as dry solids per pound of immobilized glucose isomerase are preferred. As used herein, one glucose isomerase unit is defined as the amount of glucose isomerase that will convert one micromole of glucose to fructose per minute in a solution containing two moles of glucose/liter, 0.02 moles of magnesium sulfate/liter and 0.001 mole of cobalt chloride/liter at a pH of 6.85 (0.2 M sodium maleate) at 60° C. Assay for D-glucose isomerase is done at 70° C. with 5 percent D-glucose solution containing 2 mM cobalt chloride hexahydrate ($CoCl_2.6H_2O$) and 50 mM magnesium sulfate heptahydrate ($MgSO_4.7H_2O$). After appropriate dilution (0–50 μg fructose/ml) the fructose concentration produced by the isomerase is determined by the cysteine-carbazole reaction at 60° C. for 10 minutes. See *J. Biol. Chem.* 192, 583 (1951) and *Science* 125, 648 (1957). A control stopped with 7 percent perchlorate is run to determine background levels of glucose in the sample.

The conditions under which the isomerization may be carried out may show wide variation, although operable temperature and pH ranges generally vary from about 45° C. to about 85° C. and from about pH 6 to about 8.5, respectively; more preferably the process is carried out at a temperature of from about 50° C. to about 75° C. and at a pH of from about 6.5 to about 7.5.

Thermal stabilizing agents may be added to the syrup to inhibit the inactivation of the isomerase at the elevated temperature used to improve the efficiency of the process. Multivalent cations which are commonly used as thermal stabilizers and/or cofactors include cobalt, magnesium and manganese ions. Optimal quantities of these ions may be readily determined by comparing the optimal temperature for isomerization to different concentrations of the thermal stabilizer and/or cofactor followed by an assay to determine the percent retention of isomerase activity after a given time period.

The present invention will be further illustrated with the following examples; however, these examples should not be interpreted as a limitation upon the scope of the present invention.

EXAMPLE 1

As noted above, a new species of Ampullariella, named Ampullariella species 3876 ATCC 31351 has been discovered. This species along with strains from the known species within the genus are capable of producing glucose isomerase. Ampullariella species 3876 is characterized morphologically by sporangia with irregular contours having a shape varying from oval to bottle shaped which vary in size from about 9 to 11 microns wide to about 14 to 18 microns long. Aerial mycelia are always absent, however, in some media the sporangial mass takes up the appearance of an aerial mycelium.

The cultural properties of Ampullariella species 3876 ATCC 31351 on different media suggested by Shirling and Gottlieb in *Int. J. Syst. Bacterial.* 16, pages 313–340 (1966) and Waksman in the *Actinomycetes,* Vol. 2 (Williams and Wilkins Co., Baltimore 1966) pages 328–334 are shown in Table 1. The cultural characteristics were determined after 6 to 14 days of incubation at 30° C.

TABLE 1

| The Number Accompanying Some of the Culture Media Refers to Those Given By Shirling and Gottlieb | |
|---|---|
| Culture Media | Cultural Characteristics |
| Medium n°2 (yeast extract - malt agar) | Abundant growth, crusty surface orange to 10 E6* |
| Medium n°3 (oatmeal agar) | Moderate growth, crusty surface orange light |
| Medium n°4 (inorganic salts starch agar) | Abundant growth, crusty surface orange |
| Medium n°5 (glycerol asparagine agar) | Abundant growth, smooth surface light orange 10 J 7* |
| Medium n°6 (peptone yeast extract iron agar) | Moderate growth, smooth surface |

TABLE 1-continued

The Number Accompanying Some of the Culture Media
Refers to Those Given By Shirling and Gottlieb

| Culture Media | Cultural Characteristics |
|---|---|
| Medium n°7 (tyrosine agar) | brown, deep brown pigment Abundant growth, crusty surface orange, light brown pigment |
| Oatmeal agar (according to Waksman) | Abundant growth, wrinkled surface orange 10 I 8* yellowish pigment |
| Hickey and Tresner's agar | Moderate growth, wrinkled surface brown, light brown pigment |
| Czapek glucose agar | Abundant growth, crusty surface orange 11 E 6* |
| Glucose asparagine agar | Abundant growth, crusty surface orange 9 K 9* |
| Nutrient agar | Moderate growth, smooth surface brown, light brown pigment |
| Potato agar | Abundant growth, wrinkled surface brown, brown pigment |
| Bennett's agar | Abundant growth, wrinkled surface amber-brown |
| Calcium malate agar | Very scant growth, smooth surface hyaline |
| Skim milk agar | Abundant growth, wrinkled surface brown 15 C 12* |
| Czapek agar | Scant growth, smooth surface light orange |
| Egg agar | Moderate growth, smooth surface light orange |
| Peptone glucose agar | Moderate growth, crusty surface orange to reddish 4 H 10* brown pigment |
| Agar | Very scant growth, hyaline |
| Loeffler serum | Very scant growth |
| Potato | Abundant growth, wrinkled surface orange to brown, brown pigment |
| Gelatin | Scant growth, cream to light orange |
| Cellulose agar | Very scant growth, thin, hyaline |

*Index numbers refer to A Dictionary of Color, edited by A. Maerz and M. Rea Paul (McGraw-Hill, 1950).

Table 2 compares the ability of Ampullariella species 3876 ATCC 31351 and the known species to utilize carbon sources according to the method of Pridham et al. (*Intern. J. Syst. Bact.* 56, 107, 1948). Table 3 compares physiological characteristics of the various species of Ampullariella.

From the morphological characteristics (namely the predominantly cylindrical sporangia, the rod-shaped spores, and the arrangement of the spores end to end in longitudinal rows within the sporangium) strain ATCC 31351 is recognized as a member of the genus Ampullariella. However, the cultural characteristics, the pattern of pigmentation on different agars, the physiological characteristics (namely failure to form $H_2S$, to reduce nitrate and ability to peptonize litmus milk) and the pattern of carbon compound utilization (namely the ability to grow on the complex carbohydrate raffinose) separate this strain from any of the previously known species.

TABLE 2

| MINIMAL MEDIUM CARBON COMPOUND UTILIZATION | Species 3876* | A. digitata* | A. lobata* | A. campanulata* | A. regularis* |
|---|---|---|---|---|---|
| Inositol | − | No growth | No growth | − | − |
| Fructose | + | No growth | No growth | − | + |
| Rhamnose | + | No growth | No growth | + | + |
| Mannitol | + | No growth | No growth | + | − |
| Xylose | + | No growth | No growth | + | + |
| Raffinose | + | No growth | No growth | − | − |
| Arabinose | + | No growth | No growth | + | + |
| Cellulose | − | No growth | No growth | − | − |
| Sucrose | + | No growth | No growth | − | + |
| Glucose | + | No growth | No growth | + | + |
| Mannose | + | No growth | No growth | + | + |
| Lactose | + | No growth | No growth | − | + |
| Salicin | + | No growth | No growth | − | + |

* + represents growth
− represents no growth

TABLE 3

| | Species 3876 | A. digitata | A. lobata | A. campanulata | A. regularis |
|---|---|---|---|---|---|
| CULTURAL CHARACTERISTICS | | | | | |
| Vegetative mycelium | orange to brown | brown | orange | deep orange | orange |

TABLE 3-continued

| | Species 3876 | A. digitata | A. lobata | A. campanulata | A. regularis |
|---|---|---|---|---|---|
| Pigment | (some media) brown on various agar | brown (N.6–7) agar | absent | (brown in Czapek agar) absent | yellow (oatmeal) agar |
| PHYSIOLOGICAL CHARACTERISTICS* | | | | | |
| Hydrolysis of starch | + | + | + | + | + |
| H₂S formation | − | + | + | + | + |
| Melanin production | + | + | − | − | − |
| Tyrosine reaction | − | − | − | − | − |
| Casein hydrolysis | − | − | + | − | − |
| Solubilization of calcium malate | − | − | − | − | − |
| Nitrate reduction | − | + | + | + | + |
| Liquefaction of gelatine | ± | ± | − | − | − |
| Litmus milk { coagulation | − | + | − | − | − |
| Litmus milk { peptinization | + | − | − | − | − |
| Cellulose decomposition | − | − | − | − | − |

*+ strongly positive
− strongly negative
± weakly positive

In addition to Ampullariella species 3876, three other new isolates which each represent new species within the genus have been found to produce glucose isomerase. These isolates are designated as Ampullariella species 3877 (ATCC 31352), Ampullariella species 3965 (ATCC 31353), and Ampullariella species 3966 (ATCC 31354).

The utilization of carbon sources for each of these above species is shown in Table 4. The physiological characteristics of the new species are shown in Table 5.

TABLE 4

| MINIMAL MEDIUM CARBON COMPOUND UTILIZATION | Ampullariella species | | |
|---|---|---|---|
| | 3877* | 3695* | 3966* |
| Inositol | − | − | − |
| Fructose | + | + | + |
| Rhamnose | + | + | + |
| Mannitol | + | + | + |
| Xylose | + | + | + |
| Raffinose | − | − | + |
| Arabinose | + | + | + |
| Cellulose | − | − | − |
| Sucrose | + | + | + |
| Glucose | + | + | + |
| Mannose | + | + | + |
| Lactose | − | + | + |
| Salicin | + | + | + |

*+ Represents growth
− Represents no growth

TABLE 5

| PHYSIOLOGICAL CHARACTERISTICS* | Ampullariella species | | |
|---|---|---|---|
| | 3877 | 3965 | 3966 |
| Hydrolysis of starch | + | + | + |
| H₂S formation | + | + | + |
| Melanin production | + | + | + |
| Tyrosine reaction | − | − | − |
| Casein hydrolysis | − | − | − |
| Solubilization of calcium malate | − | − | − |
| Nitrate reduction | − | − | − |
| Liquefaction of gelatine | ± | ± | ± |
| Litmus milk { coagulation | − | − | − |
| Litmus milk { peptonization | + | − | − |
| Cellulose decomposition | − | − | − |

*+ represents strongly positive
− represents strongly negative
± represents weakly positive

EXAMPLE 2

A nutrient broth generally suitable for the maintenance of Ampullariella cultures is as follows:

| 3 grams | beef extract |
|---|---|
| 5 grams | peptone |
| 1 liter | distilled water |

For the production of glucose isomerase, an Emerson xylose growth media was found to be satisfactory. The ingredients are as follows:

| 4.0 grams | beef extract |
|---|---|
| 4.0 grams | peptone |
| 2.5 grams | sodium chloride |
| 1.0 gram | yeast extract |
| 10.0 grams | xylose |
| 1.0 liter | distilled water |

EXAMPLE 3

Two ml of a nutrient broth culture of Ampullariella species 3966 was used as inoculum in a 500 ml baffled flask containing 100 ml of Emerson xylose growth medium. The culture was incubated three days at 30° C. on a shaker. The cells were harvested by centrifugation at 16,300×g for 3 minutes and washed with 100 ml of 0.013 M phosphate buffer, pH 7.0. The cells were centrifuged a second time at 27,000×g for 30 minutes. The button of wet cells was resuspended in 0.05 M Tris-HCl buffer, pH 7.4 at a concentration of 10 ml buffer per gram of wet cells. The cells were ruptured at a temperature of 4° C. using a Branson Sonifier ® Cell Disruptor producing two, three-minute pulses with a three-minute rest between pulses. Cellular debris was removed by centrifugation at 27,000×g for 30 minutes. A sample of the crude extract was assayed for glucose isomerase activity by treating a 5% glucose solution with the extract and testing for the presence of fructose using the method described hereinbefore. The extract was found to contain 0.69 glucose isomerase units per milliliter of extract.

A second sample of the extract was heated for 24 hours at 75° C. Assay of the heated sample showed 0.54 glucose isomerase units per milliliter indicating the extract retained about 78 percent of the original glucose isomerase activity of the unheated control.

EXAMPLE 4

Ampullariella species 3876 (130 wet grams) grown in a 14 liter New Brunswick fermenter with Emerson xylose medium was harvested by centrifugation. The cells were washed with distilled deionized water and centrifuged at 4° C., 27,000×g for 30 minutes. The pellet of wet cells was resuspended in 0.025 m Tris-HCl buffer, pH 7.4 containing 0.5 mM cobalt chloride at a concentration of 5 ml buffer per gram of wet cells. The cells were ruptured at 4° C. using a Branson Sonifier ® Cell Disruptor at 50 watts to produce five three-minute pulses with a three-minute rest between pulses. Cellular debris was removed by centrifugation at 27,000×g for 30 minutes. A sample of the crude extract was assayed for glucose isomerase activity and protein concentration. The sample was found to contain 1.59 glucose isomerase units per milliliter of extract, and 5.6 mg protein per milliliter of extract (0.283 glucose isomerase units per milligram protein).

Crude glucose isomerase was concentrated two-fold by rotary evaporation at 48° C. and purified two-fold (to 0.580 glucose isomerase units per milligram protein) by heating at 70° C. for one hour at 150 rpm; centrifugation at 78,480×g, 4° C. for 30 minutes removed precipitated protein from the isomerase-containing supernatant. Exhaustive dialysis of the isomerase against 0.05 M Tris-HCl, pH 7.4 was done to remove cobalt from the enzyme.

Assay of the final enzyme product using the method described in Example 3 above, showed 2.67 glucose isomerase units per milliliter. Samples of the enzyme which were heated at 75° C. for 6 and 24 hours retained 112 percent and 104 percent, respectively, of their original activity as compared to a glucose isomerase unheated control.

We claim:

1. A process for producing glucose isomerase from a microorganism belonging to the genus Ampullariella which comprises growing the Ampullariella in a culture medium and recovering the glucose isomerase therefrom.

2. The process of claim 1 wherein the culture medium contains xylose or a xylose supplying source.

3. The process of claim 1 wherein the microorganism is *Ampullariella digitata* or a mutant thereof.

4. The process of claim 1 wherein the microorganism is Ampullariella species 3876 or a mutant thereof.

5. The process of claim 1 wherein the microorganism is Ampullariella species 3877 or a mutant thereof.

6. The process of claim 1 wherein the microorganism is Ampullariella species 3965 or a mutant thereof.

7. The process of claim 1 wherein the microorganism is Ampullariella species 3966 or a mutant thereof.

8. The process of claim 1 wherein the microorganism is *Ampullariella lobata* or a mutant thereof.

9. The process of claim 1 wherein the microorganism is *Ampullariella campanulata* or a mutant thereof.

10. The process of claim 1 wherein the microorganism is *Ampullariella regularis* or a mutant thereof.

11. A process for isomerizing D-glucose to D-fructose including the step of treating the D-glucose in an aqueous medium with an isomerase produced by a microorganism belonging to the genus Ampullariella thereby converting a portion of the glucose to fructose.

12. The process of claim 11 wherein a thermal stabilizing agent is present during the isomerization.

13. The process of claim 12 wherein the thermal stabilizing agent is a cation selected from the group consisting of cobalt, magnesium, and manganese ions.

14. The process of claim 13 wherein the glucose isomerase is immobilized on a water-insoluble support.

15. The process of claim 14 wherein about one pound of immobilized glucose isomerase is present for the isomerization of from about 50 to 5000 pounds of glucose/fructose mixture as dry solids.

16. The process of claim 15 wherein the pH is from about 6 to about 8.5 and the temperature is from about 45° C. to about 85° C.

17. The process of claim 11, wherein fructose comprises between about 40 percent and 50 percent of the hexose present in the aqueous medium following treatment with glucose isomerase.

18. A biologically pure culture of the microorganism Ampullariella species 3876 demonstrating glucose isomerase activity having the identifying characteristics of ATCC 31351, said culture producing glucose isomerase in a recoverable quantity upon fermentation in an aqueous nutrient medium containing assimilable sources of carbon, nitrogen, and essential minerals.

19. A biologically pure culture of the microorganism Ampullariella species 3877 demonstrating glucose isomerase activity having the identifying characteristics of ATCC 31352, said culture producing glucose isomerase in a recoverable quantity upon fermentation in an aqueous nutrient medium containing assimilable sources of carbon, nitrogen, and essential minerals.

20. A biologically pure culture of the microorganism Ampullariella species 3965 demonstrating glucose isomerase activity having the identifying characteristics of ATCC 31353, said culture producing glucose isomerase in a recoverable quantity upon fermentation in an aqueous nutrient medium containing assimilable sources of carbon, nitrogen, and essential minerals.

21. A biologically pure culture of the microorganism Ampullariella species 3966 demonstrating glucose isomerase activity having the identifying characteristics of ATCC 31354, said culture producing glucose isomerase in a recoverable quantity upon fermentation in an aqueous nutrient medium containing assimilable sources of carbon, nitrogen, and essential minerals.

22. A culture medium consisting essentially of a biologically pure microorganism selected from the group consisting of Ampullariella species 3876, Ampullariella species 3877, Ampullariella species 3965 and Ampullariella species 3966 or a mutant thereof and an aqueous nutrient culture medium containing assimilable sources of carbon, nitrogen, and essential minerals, said culture medium wherein glucose isomerase is produced in a recoverable quantity upon aerobic fermentation.

23. The culture medium of claim 22 further including from about 0.1 percent to 10 percent by weight of xylose.

24. The culture medium of claim 23 wherein the microorganism is Ampullariella species 3876 or a mutant thereof.

25. The culture medium of claim 23 wherein the microorganism is Ampullariella species 3877 or a mutant thereof.

26. The culture medium of claim 23 wherein the microorganism is Ampullariella species 3965 or a mutant thereof.

27. The culture medium of claim 23 wherein the microorganism is Ampullariella species 3966 or a mutant thereof.

* * * * *

UNITED STATES PATENT AND TRADEMARK OFFICE
CERTIFICATE OF CORRECTION

PATENT NO. : 4,308,349

DATED : December 29, 1981

INVENTOR(S) : Sharonkay E. Foley, et al

It is certified that error appears in the above-identified patent and that said Letters Patent are hereby corrected as shown below:

Column 7, Table 4, under subtitle "Ampullariella species" the second column "3695*" should read --3965*--.

Signed and Sealed this

Thirteenth Day of July 1982

[SEAL]

Attest:

GERALD J. MOSSINGHOFF

Attesting Officer

Commissioner of Patents and Trademarks